United States Patent [19]

Friebe et al.

[11] Patent Number: 4,486,442
[45] Date of Patent: Dec. 4, 1984

[54] ANTI-ALLERGY BICYCLIC PHENOL ETHERS

[75] Inventors: Walter-Gunar Friebe, Darmstadt; Wolfgang Kampe, Heddesheim; Androniki Roesch nee Apostolides, Mannheim; Wolfgang Schaumann, Heidelberg, all of Fed. Rep. of Germany

[73] Assignee: Boehringer Mannheim GmbH, Mannheim, Fed. Rep. of Germany

[21] Appl. No.: 469,856

[22] Filed: Feb. 25, 1983

[30] Foreign Application Priority Data

Mar. 13, 1982 [DE] Fed. Rep. of Germany ....... 3209271

[51] Int. Cl.³ ................ A61K 31/445; C07D 401/12; C07D 405/12; C07D 409/12
[52] U.S. Cl. .................................. 424/267; 546/196; 546/201; 546/202
[58] Field of Search .............. 546/196, 201, 202; 424/267

[56] References Cited

U.S. PATENT DOCUMENTS 4,230,850 10/1980 Briet et al. ............... 546/196 X
4,288,442 9/1981 Friebe et al. ............. 546/201 X
4,330,549 5/1982 Friebe et al. ............. 546/196 X Primary Examiner—Richard A. Schwartz
Attorney, Agent, or Firm—Felfe & Lynch

[57] ABSTRACT

The present invention provides bicyclic phenol ethers of the general formula:

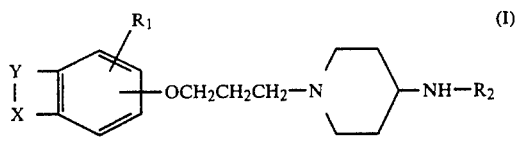

wherein
$R_1$ is a hydrogen atom or a lower alkyl radical,
$R_2$ is a hydrogen atom or an acyl radical,
X is an oxygen or sulphur atom or an —NH— group;
Y is a —CO—CHR$_3$— group or a

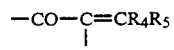

group;
$R_3$ is a hydrogen atom, a lower alkyl radical which can be optionally substituted by an aryl radical, or a cycloalkyl radical containing 3 to 7 carbon atoms; and
$R_4$ and $R_5$, which can be the same or different, are hydrogen atoms, lower alkyl radicals, lower alkyl radicals, alkenyl radicals containing 2 to 16 carbon atoms, which can be optionally substituted by an aryl radical, or an aryl radical; or
$R_4$ and $R_5$, together with the carbon atom to which they are attached, form a cycloalkyl ring containing 3 to 7 carbon atoms; and the
salts thereof with pharmacologically acceptable acids.

The present invention also provides processes for the preparation of these compounds, as well as pharmaceutical compositions containing them.

30 Claims, No Drawings

ANTI-ALLERGY BICYCLIC PHENOL ETHERS

The present invention is concerned with new bicyclic phenol ethers, with a process for the preparation thereof and with pharmaceutical compositions containing them.

The new compounds according to the present invention, as well as the pharmacologically acceptable salts thereof, have, even when administered orally in low dosages, an inhibiting action on anaphylactic reactions of the skin and of the bronchial system. A weak anti-oedematous effect has also been observed. At the same time, they also antagonise mediators liberated by allergens, for example histamine.

Compounds of similar constitution are disclosed in Federal Republic of Germany Patent Specification No. 29 01 336. We have now found that compounds which, instead of a coumarin radical, carry a benzofuran, benzothiophene or benzopyrrole radical, also display an outstanding anti-allergic action.

Thus, according to the present invention, there are provided bicyclic phenol ethers of the general formula:

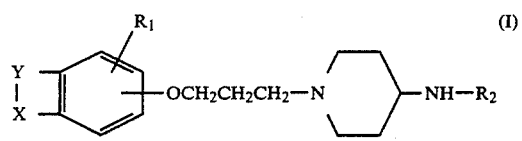

(I)

wherein $R_1$ is a hydrogen atom or a lower alkyl radical, $R_2$ is a hydrogen atom or an acyl radical, X is an oxygen or sulphur atom or an —NH— group, Y is a —CO—CHR$_3$— group or a

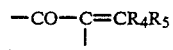

group, $R_3$ is a hydrogen atom, a lower alkyl radical, which can optionally be substituted by an aryl radical, or a cycloalkyl radical containing 3 to 7 carbon atoms and $R_4$ and $R_5$, which can be the same or different, are hydrogen atoms, lower alkyl radicals, alkenyl radicals containing 2 to 16 carbon atoms, which can optionally be substituted by an aryl radical, or an aryl radical or $R_4$ and $R_5$, together with the carbon atom to which they are attached, form a cycloalkyl ring containing 3 to 7 carbon atoms; and the salts thereof with pharmacologically acceptable acids.

The present invention also provides pharmaceutical compositions with a content of compounds of general formula (I) and is also concerned with the use of compounds of general formula (I) for the preparation of such compositions.

When $R_1$, $R_3$, $R_4$ and $R_5$ represent lower alkyl radicals, these contain up to 6 and preferably up to 4 carbon atoms and can be straight-chained or branched, methyl, isopropyl and n-propyl radicals being preferred. When $R_4$ and $R_5$ represent alkenyl radicals, these can be straight-chained, branched or cyclic and can contain up to 3 double bonds, preferred radicals of this type including the farnesyl, geranyl and (2,6,6-trimethylcyclohex-1-en-1-yl)-vinyl radicals. An alkenyl radical substituted by aryl is preferably a styryl radical.

The aryl radicals present in $R_3$, $R_4$ and $R_5$ are preferably phenyl radicals which, if desired, can be substituted by halogen, lower alkyl or lower alkoxy. The acyl radicals of the substituent $R_2$ are lower alkanoyl radicals containing up to 5 carbon atoms which, if desired, can be substituted by optionally substituted aryl (e.g. phenacetyl), or are lower alkenoyl radicals containing 3 to 6 carbon atoms, which are optionally substituted by aryl (e.g. cinnamoyl), or are aroyl radicals which can optionally be substituted by halogen, hydroxyl, lower alkyl, lower alkoxy, nitro, amino, lower alkylthio, lower alkylsulphinyl, lower alkylsulphonyl or cyano.

The lower alkyl moieties in all of the mentioned radicals contain up to 6 and preferably up to 4 carbon atoms and can be straight-chained or branched. Aroyl radicals can be, for example, benzoyl or naphthoyl radicals.

Furthermore, $R_2$ can represent the acid residue of a carbocyclic carboxylic acid containing 4 to 8 carbon atoms. The expression aryl in the definition of the substituent $R_2$ preferably means phenyl or naphthyl, optionally substituted by halogen, lower alkyl, lower alkoxy, amino or nitro. The halogen atoms can be fluorine, chlorine or bromine.

The basic structures which X and Y can form with the phenyl moiety are cumaran-2-one, cumaran-3-one, oxindole and thianaphthen-3-one.

As a rule, the oxypropyl group is in the 4-, 5- or 6-position of the ring system in question.

Apart from the compounds mentioned in the following specific Examples, the present invention also provides, in particular, all compounds which have every possible combination of the substituents mentioned in the Examples.

The process according to the present invention for the preparation of compounds of general formula (I) is characterised in that, in per se known manner, a compound of the general formula:

(II)

in which $R_1$, X and Y have the above-given meanings, is reacted with a compound of the general formula:

(III), in which L and M signify reactive residues, and with a compound of the general formula:

(IV)

in which $R_2$ has the above-given meaning, whereafter, if desired, the group $R_2$ is converted in known manner into another group $R_2$, when $R_3$ signifies a hydrogen atom, the product is, if desired, condensed with a compound of the general formula $R_4$.CO.$R_5$, in which $R_4$ and $R_5$ have the above-given meanings, or with a reactive derivative thereof, when Y signifies a

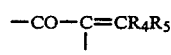

group, if desired the double bond is reduced; and the reaction product obtained is, if desired, converted into a pharmacologically acceptable salt.

The reactive residues L and M in compounds of general formula (III) are preferably chlorine or bromine atoms or mesyloxy or tosyloxy radicals.

The process according to the present invention can be carried out, for example, by first condensing a compound of general formula (III) with a compound of general formula (IV), followed by isolation of the reaction product obtained. This intermediate is then reacted with a compound of general formula (II). The reaction is preferably carried out in an alkaline medium, for example in a lower alcohol, such as isopropanol, in the presence of sodium isopropanolate, or in dimethylformamide or tetrahydrofuran in the presence of potassium carbonate or triethylamine.

According to another variant of the process, a compound of general formula (II) is first reacted with a compound of general formula (III), whereafter the reaction product obtained is reacted with a compound of general formula (IV) to give the desired end product of general formula (I).

A subsequent conversion of a group $R_2$ in a compound of general formula (I) into another group $R_2$ can take place, for example, by the acylation of a compound of general formula (I) in which $R_2$ is a hydrogen atom with a compound of the general formula $R_2.Z$, in which Z is a reactive residue. Consequently, compounds of general formula (I) in which $R_2$ is a hydrogen atom are valuable intermediates for the preparation of other compounds of general formula (I). Reactive residues Z can be all residues which are used in peptide chemistry for the activation of carboxylic acids, for example halogen atoms, the azide group and alkoxy, aryloxy and acyloxy radicals.

According to a further possibility for the subsequent conversion of $R_2$ in compounds of general formula (I), one or more substituents of the acyl radical $R_2$ are converted by generally known processes into one or more other substituents of the acyl radical $R_2$, for example by esterification, saponification, reduction, alkylation, acylation, hydrogenolysis, oxidation, amidation or elimination.

A possibly desired condensation of a compound of general formula (I), in which $R_3$ is a hydrogen atom, with a carbonyl compound of the general formula $R_4.CO.R_5$ or with a reactive derivative thereof preferably takes place in an organic solvent in the presence of an agent splitting off water, for example in a lower alcohol or in toluene in the presence of potassium hydroxide or ammonia or toluenesulphonic acid.

When Y represents a

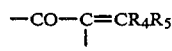

radical, a reduction thereof can be carried out, for example, with catalytically activated hydrogen in the presence of a noble metal catalyst, for example palladium or platinum.

The starting compounds of general formulae (II), (III) and (IV) are either known from the literature or can be prepared analogously to processes known from the literature.

The pharmacologically acceptable salts are obtained in the usual manner, for example by neutralising compounds of general formula (I) with non-toxic inorganic or organic acids, for example hydrochloric acid, sulphuric acid, phosphoric acid, hydrobromic acid, acetic acid, lactic acid, citric acid malic acid, salicylic acid, malonic acid or succinic acid.

For the preparation of pharmaceutical compositions, the compounds of general formula (I) are mixed in known manner with appropriate pharmaceutical carrier substances, aroma, flavouring and colouring materials and formed, for example, into tablets or dragees or, with the addition of appropriate adjuvants, suspended or dissolved in water or an oil, for example, olive oil.

The compounds of general formula (I) can be administered orally and parenterally in liquid or solid form. As injection medium, it is preferred to use water which contains the stabilising agents, solubilising agents and/or buffers conventional for injection solutions. Additives of this kind include, for example, tartrate and borate buffers, ethanol, dimethyl sulphoxide, complex formers (such as ethylenediamine-tetraacetic acid), high molecular weight polymers (such as liquid polyethylene oxide) for viscosity regulation and polyethylene derivatives of sorbitan anhydrides.

Solid carrier materials can be, for example, starch, lactose, mannitol, methyl cellulose, talc, highly dispersed silicic acid and high molecular weight polymers (such as polyethylene glycols).

Compositions suitable for oral administration can, if desired, contain flavouring and/or sweetening agents. For external use, the compounds of general formula (I) according to the present invention can also be used in the form of powders and salves. For this purpose, they are mixed, for example, with powdered, physiologically compatible diluents or conventional salve bases.

The dosage administered depends upon the age, the state of health and the weight of the recipient, upon the extent of the disease, the nature of possibly simultaneously administered other treatments, the frequency of the treatment and the nature of the desired effect. Usually, the daily dosage of the active compound is from 0.1 to 50 mg./kg. of body weight. Normally, 0.5 to 40 and preferably 1.0 to 20 mg./kg./day in one or more administrations per day are effective in order to obtain the desired results.

Apart from the compounds mentioned in the following Examples, according to the present invention, the following compounds are also preferred:

6-[3-(4-benzamidopiperidino)-propoxy]-2-isopropylidenebenzo[b]thiophen-3-one;

6-[3-(4-phenylacetamidopiperidino)-propoxy]-2-isopropylidene-benzo[b]thiophen-3-one; and 6-{3-[4-(2-nitrobenzamido)-piperidino]-propoxy}-2-isopropylidene-benzo[b]thiophen-3-one.

The following Examples are given for the purpose of illustrating the present invention:

EXAMPLE 1

6-[3-(4-Benzamidopiperidino)-propoxy]-2-cyclohexylidene-cumaran-3-one 6.1 g. (25 mMole) 2-Cyclohexylidene-6-hydroxycumaran-3-one are added at 40° C. to a solution of 0.58 g. (25 mMole) sodium in 75 ml. propan-2-ol. The reaction mixture is stirred for 10 minutes at 40° C., 8.4 g. (30 mMole) 3-(4-benzamidopiperidino)-propyl chloride are added thereto, the reaction mixture is heated under reflux for 6 hours, then cooled and the precipitate obtained is separated off and recrystallised from ethanol.

There are obtained 8.7 g. (75% of theory) 6-[3-(4-benzamidopiperidino)-propoxy]-2-cyclohexylidene-cumaran-3-one; m.p. 174°–175° C.

The 2-cyclohexylidene-6-hydroxycumaran-3-one used as starting material can be obtained as follows:

A mixture of 20.0 g. (0.13 mole) 6-hydroxycumaran-3-one, 60 ml. cyclohexanone, 600 ml. ethanol and 50 g. potassium hydroxide is stirred for 36 hours at ambient temperature, filtered and the filtrate acidified with hydrochloric acid. 11.7 g. (40% of theory) 2-cyclohexylidene-6-hydroxycumaran-3-one thereby precipitate out; m.p. 210°–212° C.

EXAMPLE 2

The following compounds are obtained in a manner analogous to that described in Example 1:

| designation | yield % | m.p. °C. (solvent) |
| --- | --- | --- |
| (a) 5-[3-(4-benzamido-piperidino)-propoxy]-3-isopropylideneoxindole from 5-hydroxy-3-isopropylideneoxindole and 3-(4-benzamidopiperidino)-propyl chloride | 36 | 205 (diethyl ether) |
| (b) 5-{3-[4-(4-fluorobenzamido)-piperidino]-propoxy}-3-isopropylideneoxindole from 5-hydroxy-3-isopropylideneoxindole and 3-[4-(4-fluorobenzamido)-piperidino]-propyl chloride | 24 | 214 (diethyl ether) |
| (c) 5-{3-[4-(3-methylbenzamido)-piperidino]-propoxy}-3-isopropylideneoxindole from 5-hydroxy-3-isopropylideneoxindole and 3-[4-(3-methylbenzamido)-piperidino]-propyl chloride | 13 | 182–184 (diethyl ether) |
| (d) 5-{3-[4-(2-methoxybenzamido)-piperidino]propoxy}-3-isopropylideneoxindole from 5-hydroxy-3-isopropylideneoxindole and 3-[4-(2-methoxybenzamido)-piperidino]-propyl chloride | 18 | 172 (propan-3-ol) |
| (e) 6-[3-(4-benzamido-piperidino)-propoxy]-3-isopropylidenecumaran-2-one from 6-hydroxy-3-isopropylidenecumaran-2-one and 3-(4-benzamidopiperidino)-propyl chloride | 42 | 167 (diethyl ether) |
| (f) 6-[3-(4-cyclopropane-carboxamidopiperidino)-propoxy]-2-isopropylidene-cumaran-3-one from 6-hydroxy-2-isopropylidenecumaran-3-one and 3-(4-cyclopropanecarboxamidopiperidino)-propyl chloride | 45 | 165–167 (diethyl ether) |
| (g) 6-[3-(4-benzamido-piperidino)-propoxy]-2-isopropylidenecumaran-3-one from 6-hydroxy-2-isopropylidenecumaran-3-one and 3-(4-benzamidopiperidino)-propyl chloride | 70 | 187–189 (propan-2-ol) |
| (h) 4-{3-[4-(4-fluorobenzamido)-piperidino]-propoxy}-2-isopropylidenecumaran-3-one from 4-hydroxy-2-isopropylidenecumaran-3-one and 3-[4-(4-fluorobenzamido)-piperidino]-propyl chloride | 54 | 194 (methanol) |
| (i) 6-{3-[4-(4-fluorobenzamido)-piperidino]-propoxy}-2-isopropylidenecumaran-3-one from 6-hydroxy-2-isopropylidenecumaran-3-one and 3-[4-(4-fluorobenzamido)-piperidino]-propyl chloride | 56 | 175 (methanol/diethyl ether) |
| (j) 6-{3-[4-(2-nitrobenzamido)-piperidino]-propoxy}-2-isopropylidenecumaran-3-one from 6-hydroxy-2-isopropylidenecumaran-3-one and 3-[4-(2-nitrobenzamido)-piperidino]-propyl mesylate | 26 | 169 (diethyl ether) |
| (k) 6-{3-[4-(2-methylthiobenzamido)-piperidino]-propoxy}-2-isopropylidenecumaran-3-one from 6-hydroxy-2-isopropylidenecumaran-3-one and 3-[4-(2-methylthiobenzamido)-piperidino]-propyl mesylate | 20 | 140 (diethyl ether) |
| (l) 6-{3-[4-(2-methanesulphonylbenzamido)-piperidino]-propoxy}-2-isopropylidenecumaran-3-one from 6-hydroxy-2-isopropylidenecumaran-3-one and 3-[4-(2-methanesulphonylbenzamido)-piperidino]-propyl mesylate | 29 | 160 (ethyl acetate) |
| (m) 6-{3-[4-(2-nitrophenylacetamido)-piperidino]-propoxy}-2-isopropylidenecumaran-3-one from 6-hydroxy-2-isopropylidenecumaran-3-one and 3-[4-(2-nitrophenylacetamido)-piperidino]-propyl mesylate | 18 | hydrochloride 80–85 (ethyl acetate) |
| (n) 2-isopropylidene-6-[3-(4-phenylacetamidopiperidino)-propoxy]-7-propylcumaran-3-one from 6-hydroxy-2-isopropylidene-7-propylcumaran-3-one and 3-(4-phenylacetamidopiperidino)-propyl chloride | 53 | 159–161 (diethyl ether) |
| (o) 6-[3-(4-benzamidopiperidino)-propoxy]-2-(1-geranyl-2-propylidene)-cumaran-3-one from 2-(1-geranyl-2-propylidene)-6-hydroxycumaran-3-one and 3-(4-benzamidopiperidino)-propyl chloride | 51 | amorphous (ligroin) |
| (p) 6-[3-(4-benzamidopiperidino)-propoxy]-2-[4-(2,6,6-trimethylcyclohex-1-en-1-yl)-3-buten-2-yliden]-cumaran-3-one from 6-hydroxy-2-[4-(2,6,6-trimethylcyclohex-1-en-1-yl)-3-buten-2-yliden]-cumaran-3-one and 3-(4-benzamidopiperidino)-propyl chloride | 35 | amorphous (ligroin) |
| (q) 6-[3-(4-benzamidopiperidino)-propoxy]-2-(1-farnesyl-2-propylidene)-cumaran-3-one from 2-(1-farnesyl-2-propylidene)-6-hydroxycumaran-3-one and 3-(4-benzamidopiperidino)-propyl chloride | 32 | oxalate 80 (ethyl acetate) |
| (r) 6-[3-(4-benzamidopiperidino)-propoxy]-2-(2-methyl-1-propylidene)-cumaran-3-one from 6-hydroxy-2-(2-methyl-1-propylidene)-cumaran-3-one and 3-(4-benzamidopiperidino)-propyl chloride | 44 | 93 (propan-2-ol) |
| (s) 6-[3-(4-benzamidopiperidino)-propoxy]-2-cinnamylidene-cumaran-3-one from 2-cinnamylidene-6-hydroxycumaran-3-one and 3-(4-benzamidopiperidino)-propyl | 60 | 178–180 (ethanol) |

| designation | yield % | m.p. °C. (solvent) |
|---|---|---|
| propyl chloride | | |
| (t) 6-[3-(4-benzamidopiperidino)-propoxy]-2-benzylidene-cumaran-3-one from 2-benzylidene-6-hydroxycumaran-3-one and 3-(4-benzamidopiperidino)-propyl chloride | 78 | 214–216 (methanol) |
| (u) 2-benzylidene-6-{3-[4-(4-fluorobenzamido)-piperidino]-propoxy}-cumaran-3-one from 2-benzylidene-6-hydroxycumaran-3-one and 3-[4-(4-fluorobenzamido)-piperidino]-propyl chloride | 48 | 183–185 (propan-2-ol) |
| (v) 6-[3-(4-phenylacetamido-piperidino)-propoxy]-7-propylcumaran-3-one from 6-hydroxycumaran-3-one and 3-(4-phenylacetamido-piperidino)-propyl chloride | 49 | 145–146 (diethyl ether) |

EXAMPLE 3

6-{3-[4-(2-Aminobenzamido)-piperidino]-propoxy}-2-isopropylidene-cumaran-3-one

A mixture of 9.8 g. (31 mMole) 6-(3-bromopropoxy)-2-isopropylidene-cumaran-3-one, 6.9 g. (31 mMole) 4-(2-aminobenzamido)-piperidine, 10.1 g. (0.1 mole) triethylamine and 100 ml. tetrahydrofuran is heated under reflux for 16 hours. The reaction mixture is then evaporated and the residue is taken up in dichloromethane, washed until neutral, evaporated and the residue chromatographed on silica gel (elution agent dichloromethane/methanol 9:1 v/v). After triturating with diethyl ether, there are obtained 4.9 g. (35% of theory) 6-{3-[4-(2-aminobenzamido)-piperidino]-propoxy}-2-isopropylidene-cumaran-3-one; m.p. 139°–140° C.

The 6-(3-bromopropoxy)-2-isopropylidene-cumaran-3-one used as starting material can be prepared as follows:

20.0 g. (0.15 mole) potassium carbonate are added at 75° C., in the course of 3 hours, to a solution of 25.0 g. (0.13 mole) 6-hydroxy-2-isopropylidene-cumaran-3-one and 40 ml. 1,3-dibromopropane in 130 ml. butanone. The reaction mixture is heated under reflux for 48 hours, then filtered and the filtrate evaporated, the residue obtained being triturated with ligroin. There are thus obtained 29.8 g. (74% of theory) 6-(3-bromopropoxy)-2-isopropylidene-cumaran-3-one; m.p. 80°–82° C.

EXAMPLE 4

The following compounds are obtained in a manner analogous to that described in Example 3:

| designation | Yield % | m.p. °C. (solvent) |
|---|---|---|
| (a) 2-isopropylidene-6-[3-(4-phenylacetamidopiperidino)-propoxy]-cumaran-3-one from 6-(3-bromopropoxy)-2-isopropylidene-cumaran-3-one and 4-phenylacetamido-piperidine | 38 | 150 (propan-2-ol) |
| (b) 6-[3-(4-aminopiperidino)-propoxy]-2-isopropylidene-cumaran-3-one from 6-(3-bromopropoxy)-2-isopropylidene-cumaran-3-one and 4-aminopiperidine | 83 | hydrochloride amorphous (diethyl ether) |

EXAMPLE 5

6-[3-(4-Benzamidopiperidino)-propoxy]-2-isopropyl-cumaran-3-one

A solution of 5.0 g. (11 mMole) 6-[3-(4-benzamidopiperidino)-propoxy]-2-isopropylidene-cumaran-3-one (see Example 2g) in 200 ml. methanol is hydrogenated at ambient temperature and 1 bar hydrogen pressure in the presence of 0.5 g. platinum oxide. After taking up the calculated amount of hydrogen, the reaction mixture is filtered, the filtrate is evaporated and the residue is recrystallised from propan-2-ol. There are obtained 3.6 g. (75% of theory) 6-[3-(4-benzamidopiperidino)-propoxy]-2-isopropylcumaran-3-one; m.p. 146°–147° C.

EXAMPLE 6

The following compounds are obtained in a manner analogous to that described in Example 5:

| designation | Yield % | m.p. °C. (solvent) |
|---|---|---|
| (a) 6-[3-(4-benzamidopiperidino)-propoxy]-2-(2-methylpropyl)-cumaran-3-one from 6-[3-(4-benzamidopiperidino)-propoxy]-2-(2-methyl-1-propylidene)-cumaran-3-one (Example 2 r) | 69 | 133–135 (diethyl ether) |
| (b) 6-[3-(4-benzamidopiperidino)-propoxy]-2-(3-phenylpropyl)-cumaran-3-one from 6-[3-(4-benzamidopiperidino)-propoxy]-2-cinnamylidenecumaran-3-one (Example 2 s) | 41 | 120–122 (diethyl ether) |
| (c) 6-[3-(4-benzamidopiperidino)-propoxy]-2-cyclohexylcumaran-3-one from 6-[3-(4-benzamidopiperidino)-propoxy]-2-cyclohexylidenecumaran-3-one (Example 1) | 60 | 150 (ethyl acetate) |
| (d) 5-{3-[4-(4-fluorobenzamido)-piperidino]-propoxy}-3-isopropyloxindole from 5-{3-[4-(4-fluorobenzamido)-piperidino]-propoxy}-3-isopropylideneoxindole (Example 2 b) | 63 | hydrochloride 145 (ethyl acetate) |

EXAMPLE 7

6-[3-(4-Cyclopropanecarboxamidopiperidino)-propoxy]-2-isopropylidene-cumaran-3-one A solution of 3.65 g. (25 mMole) cyclopropanecarboxylic acid chloride in 50 ml. dichloromethane is added dropwise to a mixture of 6.6 g. (20 mMole) 6-[3-(4-aminopiperidino)-propoxy]-2-isopropylidene-cumaran-3-one (Example 4b) and 8.4 g. (0.1 mole) sodium bicarbonate in 150 ml. dichloromethane. The reaction mixture is stirred for 5 hours at ambient temperature, then washed neutral and the organic phase is evaporated. The residue is chromatographed on silica gel (elution agent dichloromethane/methanol 9:1 v/v). There is obtained 1.8 g. (23% of theory) 6-[3-(4-cyclopropanecarboxamidopiperidino)-propoxy]-2-isopropylidene-cumaran-3-one, which is identical with the compound of Example 2f.

EXAMPLE 8

2-Isopropylidene-6-[3-(4-phenylacetamidopiperidino)-propoxy]-7-propylcumaran-3-one Ammonia is passed at 20° C. into a solution of 9.0 g. (20 mMole) 6-[3-(4-phenylacetamidopiperidino)-propoxy]-7-propylcumaran-3-one (Example 2v) in 50 ml. ethanol and 10 ml. acetone up to saturation. The reaction mixture is then heated under reflux for 3 hours, evaporated and the residue chromatographed on silica gel (elution agent dichloromethane/methanol 95:5 v/v). There are obtained 4.1 g. (42% of theory) 2-isopropylidene-6-[3-(4-phenylacetamidopiperidino)-propoxy]-7-propylcumaran-3-one, which is identical with the compound of Example 2n.

EXAMPLE 9

Tablets were produced, each of which contained 10 mg. 6-[3-(4-benzamidopiperidino)-propoxy]-2-isopropylidene-cumaran-3-one. The tablets were produced according to the following formulation:

| | |
|---|---|
| 6-[3-(4-benzamidopiperidino)-propoxy]-2-isopropylidene-cumaran-3-one | 10 g |
| lactose | 80 g. |
| starch | 29 g. |
| magnesium stearate | 1 g. |

The active compound was finely powdered and mixed with lactose and starch. The mixture was granulated in conventional manner. Magnesium stearate was added to the granulate and the mixture obtained was pressed to give 1000 tablets, each having a weight of 0.12 g.

The foregoing compounds can be used as such or they can be converted to salts with pharmacologically acceptable acids. They can be administered to patients orally, as pills, tablets, capsules, powders and the like. The preferred form of oral administration is a tablet containing 10 to 300 mg of active compound, which nearly complies with the typical daily dosage. a preferred dosage is 30 to 100 mg.

The compounds can also be administered parenterally. Injection solutions containing 0.05 to 50 mg/ml of injection solution are administered.

The superior activity of the novel compounds is shown by comparing the inhibition of antigen induced bronchospasms in passively sensitized guinea pigs. Specifically, tests were run as follows:

Preparation of Antiserum

The antigen is twice recrystallized egg albumin. Equal volumes of saline solution of antigen (5 mg/ml) and Freund's complete adjuvant were emulsified and 0.15 ml injected into each hind foot of adult male guinea pigs (Davies and Johnson: Int. Arch. Allergy, 41, 648–654, 1971).

The animals were bled and the pooled serum stored at −20° C.

Passive sensitization

Injections of 0.5 ml antiserum of 1:50 dilution were given i.v. 24–48 hrs. before challenge.

Guinea pigs were anaesthetized with pentobarbitone sodium (40 mg/kg i.p.). Cannulae were tied into the trachea and the jugular vein and the lung inflated with a pump at a rate of 72 strokes/min. and a constant stroke volume of 6–8 ml.

Bronchospasm, provoked by injecting ovalbumim i.v. was measured as described by Konzett Rössler (Versuchsanordnung zu Untersuchungen an der Bronchialmuskulat Naunyn-Schmiedebergs Arch. exp. Path. Pharmak. 195, 71–74, 1940), and modified by Collier and James (Collier, H. O. J., J. A. Holgate, M. Schachter: The Bronchoconstrictor Action of Bradykinin in the Guinea-Pig, Brit. J. Pharmacol., 15, 290, 1960).

Drugs were applied p.o. 60 minutes before antigen. For calculation the following formula was used:

$$\% \text{ Bronchospasm} \frac{b-a}{m-a} \times 100$$

b = Bronchospasm after antigen injection, measured in mm from tracing
m = Maximum height of tracing in mm with arm of the trachea-cannula clamped
a = pre-injection height of the tracing in mm Percent (%) inhibition of bronchospasm was calculated by comparing control groups with drug pretreated groups 3 minutes after antigen application.

Inhibition of antigen induced bronchospasm (BrSp) in passively sensitized guinea pig

| Example | Dose (mg/kg) | Application | Inhibition of BrSp (%) |
|---|---|---|---|
| Bsp. 2 g | 3.0 | p.o. | 51 |
| Bsp. 4 a | 1.5 | p.o. | 96 |
| Bsp. 1 | 1.5 | p.o | 48 |
| Bsp. 2 a | 3.0 | p.o. | 92 |
| Bsp. 2 v | 3.0 | p.o. | 56 |
| Bsp. 6 d | 3.0 | p.o | 67 |
| Tiaramide* | 100.0 | p.o. | 0 |
| | 200.0 | p.o. | 17 |

*4-[(5-chloro-2-oxo-3(2H)—benzothiazolyl)acetyl]-1-piperazineethanole U.S. Pat. No. 3 661 921)

It will be understood that the specification and examples are illustrative but not limitative of the present invention and that other embodiments within the spirit and scope of the invention will suggest themselves to those skilled in the art.

What is claimed is:
1. A bicyclic phenol ether of the formula:

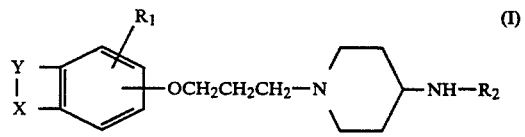

wherein
$R_1$ is a hydrogen atom or $C_1$-$C_6$ alkyl,
$R_2$ is a hydrogen atom; an acyl residue of a saturated or unsaturated $C_1$-$C_6$ aliphatic carboxylic acid which is unsubstituted or substituted one time by phenyl or phenyl substituted one time by halogen, $C_1-C_6$ alkyl, $C_1-C_6$ alkoxy, amino or nitro; an acyl residue of a $C_4-C_8$ carbocyclic carboxylic acid, phenyl carboxylic acid or phenyl carboxylic acid substituted one time by halogen, hydroxyl, $C_1-C_6$ alkyl, $C_1-C_6$ alkoxy, nitro, amino, $C_1-C_6$ alkylthio, $C_1-C_6$ alkylsulphinyl, $C_1-C_6$, alkylsulphonyl or cyano;

X is an oxygen or sulphur atom or a —NH— group;
Y is a

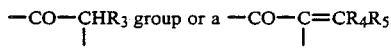

group;

R$_3$ is a hydrogen atom; a $C_3-C_7$ cycloalkyl radical; or $C_1-C_6$ alkyl which is unsubstituted or substituted one time by phenyl or phenyl substituted one time by halogen, $C_1-C_6$ alkyl or $C_1-C_6$ alkoxy; and R$_4$ and R$_5$, which are the same or different, are hydrogen; $C_1-C_6$ alkyl; a straight-chained, branched or cyclic $C_2-C_{16}$ alkenyl with 1 to 3 double bonds in the alkenyl moiety which is unsubstituted or substituted one time by phenyl or phenyl substituted one time by halogen, $C_1-C_6$ alkyl or $C_1-C_6$ alkoxy; or phenyl, or R$_4$ and R$_5$, together with the carbon atom to which they are attached, form a $C_3-C_7$ cycloalkyl ring; or a pharmacologically acceptable salt thereof.

2. The ether of claim 1 wherein R$_1$ is hydrogen.
3. The ether of claim 1 wherein R$_1$ is $C_1-C_6$ alkyl.
4. The ether of claim 1 wherein R$_2$ is hydrogen.
5. The ether of claim 1 wherein X is oxygen.
6. The ether of claim 1 wherein X is —NH—.
7. The ether of claim 1 wherein Y is

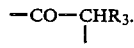

8. The ether of claim 1 wherein Y is

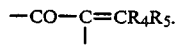

9. The ether of claim 1 wherein R$_3$ is a hydrogen atom.
10. The ether of claim 1 wherein R$_3$ is $C_1-C_6$ alkyl.
11. The ether of claim 1 wherein R$_3$ is $C_1-C_6$ alkyl substituted by phenyl which is substituted or unsubstituted by fluorine, chlorine, bromine, $C_1-C_6$ alkyl or $C_1-C_6$ alkoxy.
12. The ether of claim 1 wherein R$_3$ is $C_3-C_7$ cycloalkyl.
13. The ether of claim 1 wherein R$_4$ is a hydrogen atom.
14. The ether of claim 1 wherein R$_4$ is $C_1-C_6$ alkyl.
15. The ether of claim 1 wherein R$_5$ is $C_1-C_6$ alkyl.
16. The ether of claim 1 wherein R$_5$ is $C_2-C_{16}$ alkenyl with 1 to 3 double-bonds in the alkyl moiety.

17. The ether of claim 1 wherein R$_5$ is farnesyl, geranyl or (2,6,6-trimethylcyclohex-1-en-1-yl)-vinyl.
18. The ether of claim 1 wherein R$_5$ is styryl.
19. The ether of claim 1 wherein R$_5$ is phenyl.
20. The ether of claim 1 wherein R$_4$ and R$_5$ together with the carbon atom to which they are attached, form a $C_3-C_7$ cycloalkyl ring.
21. The ether of claim 1 wherein R$_1$, R$_3$, R$_4$ and R$_5$ are selected from the group consisting of methyl, isopropyl and n-propyl.
22. A compound according to claim 1 wherein such compound is
6-[3-(4-benzamidopiperidino)-propoxy]-2-cyclohexylidenecumaran-3-one or a pharmaceutical acceptable salt thereof.
23. A compound according to claim 1 wherein such compound is
5-[3-(4-benzamidopiperidino)-propoxy]-3-isopropylideneoxindole or a pharmaceutical acceptable salt thereof.
24. A compound according to claim 1 wherein such compound is
6-[3-(4-benzamidopiperidino)-propoxy]-2-isopropylidenecumaran-3-one or a pharmaceutical acceptable salt thereof.
25. A compound according to claim 1 wherein such compound is
6-[3-(4-phenylacetamidopiperidino)-propoxy]-7-propyl-cumaran-3-one or a pharmaceutical acceptable salt thereof.
26. A compound according to claim 1 wherein such compound is
2-isopropylidene-6-[3-(4-phenylacetamidopiperidino)-propoxy]-cumaran-3-one or a pharmaceutical acceptable salt thereof.
27. A compound according to claim 1 wherein such compound is
5-[[3-[4-(4-fluorobenzamido)-piperidino]propoxy]]-3-isoproyloxindole or a pharmaceutical acceptable salt thereof.
28. A pharmaceutical composition comprising an anti-allergically effective amount of a compound or salt according to claim 1 and a pharmacologically acceptable diluent.
29. A method of combating an allergic response in a patient which comprises administering to such a patient an anti-allergically effective amount of a compound or salt according to claim 1.
30. The method according to claim 29 wherein such compound is
6-[3-(4-benzamidopiperidino)-propoxy]-2-cyclohexylidenecumaran-3-one;
5-[3-(4-benzamidopiperidino)-propoxy]-3-isopropylideneoxindole;
6-[3-(4-benzamidopiperidino)-propoxy]-2-isopropylidenecumaran-3-one;
6-[3-(4-phenylacetamidopiperidino)-propoxy]-7-propyl-cumaran-3-one;
2-isopropylidene-6-[3-(4-phenylacetamidopiperidino)-propoxy]-cumaran-3-one; and
5-[[3-[4-(4-fluorobenzamido)-piperidino]-propoxy]]-3-isopropyloxindole or a pharmaceutical acceptable salt thereof.

* * * * *